US006691764B2

(12) United States Patent
Embert et al.

(10) Patent No.: US 6,691,764 B2
(45) Date of Patent: Feb. 17, 2004

(54) METHOD FOR PRODUCING CASTING MOLDS

(75) Inventors: Hugo Embert, Montreal (CA); Jean-Marc Perot, Mount Royal (CA)

(73) Assignee: Cynovad Inc., Ville St-Laurent (CA)

( * ) Notice: Subject to any disclaimer, the term of this patent is extended or adjusted under 35 U.S.C. 154(b) by 0 days.

(21) Appl. No.: 10/233,016

(22) Filed: Sep. 3, 2002

(65) Prior Publication Data

US 2003/0116299 A1 Jun. 26, 2003

Related U.S. Application Data

(60) Provisional application No. 60/396,720, filed on Jul. 19, 2002.

(51) Int. Cl.[7] .............................. B22C 9/02; B22D 46/00
(52) U.S. Cl. .............................. 164/4.1; 164/35; 164/45; 700/118; 433/223
(58) Field of Search ........................... 164/4.1, 35, 45; 700/118; 433/223

(56) References Cited

U.S. PATENT DOCUMENTS 5,690,490 A * 11/1997 Cannon et al. ............. 433/226
6,177,034 B1 * 1/2001 Ferrone ..................... 264/40.1
6,287,121 B1 * 9/2001 Guiot et al. ................ 433/218
6,398,554 B1 * 6/2002 Perot et al. ................. 433/223
6,460,594 B1 * 10/2002 Lam ............................ 164/35
6,506,054 B2 * 1/2003 Shoher et al. .............. 433/223

* cited by examiner

*Primary Examiner*—M. Alexandra Elve
*Assistant Examiner*—I.-H Lin
(74) *Attorney, Agent, or Firm*—James Anglehart; Ogilvy Renault

(57) ABSTRACT

There is provided a method for producing a dental prosthesis comprising: obtaining three-dimensional digital data relating to a patient's dentition; designing a virtual prosthesis for the dentition using the three-dimensional digital data; transmitting digital data corresponding to the virtual prosthesis to an automated prototyping system; producing a prototype of the dental prosthesis with the automated prototyping system, the prototype made of a material that can be ablated; covering at least the prototype with a hardening material and removing the prototype from within said hardening material to produce a mold for the dental prosthesis; casting the dental prosthesis by filling the mold with a metal and removing the hardening material.

13 Claims, 3 Drawing Sheets

METHOD FOR PRODUCING CASTING MOLDS

CROSS-REFERENCE TO RELATED APPLICATIONS

This application claims benefit of Provisional Application Serial No. 60/396,720 filed Jul. 19, 2002.

The application claims priority of Canadian Patent entitled "Method for Producing Casting Molds" having application serial number 2,356,631 and filed on Aug. 31, 2001.

FIELD OF THE INVENTION

The invention relates to the production of custom-made casting molds. More specifically, the present invention is concerned with a method used to cast molds for dental prostheses and other such molds.

BACKGROUND OF THE INVENTION

The conventional approach to produce custom casting molds has traditionally been the lost wax casting process. This process is based on the following principles:

1. A model or pattern of the desired finished product is made in wax;
2. This pattern is mounted with sprues and reservoirs to support the pattern in the desired casting position, provide passageways for wax elimination and form lines through which molten metal enters the mold;
3. This pattern is surrounded by a creamy investment plaster that hardens to form a mold;
4. This mold is heated to melt away the wax pattern that is "lost";
5. Metal is then cast into the cavity left by the "lost wax", thus duplicating the original wax pattern (the quantity of metal is calculated based on measurements of either the weight or the volume of the wax pattern);
6. The mold is then destroyed to recover the casting.

This process dates back in time beyond Egypt's pyramids. Examples of castings include the Shang Dynasty in China, 16$^{th}$ century Europe, and the Aztecs of Mexico, to name a few. These are monuments to the abilities of casters down through the ages. Today, the process is becoming even more popular because of the need for a near-finished casting.

Refinements of this process were developed by a dentist in 1907, and applied to the casting of gold inlays and dental bridgework. Today's craftsmen apply the very same techniques in making parts for models, fishing lures, specialised machine components and endless pieces of jewellery.

Since every detail created in the surface of the finished wax model will ultimately be re-created in metal when the casting is complete, special care taken in making the wax pattern can minimise the finishing and polishing steps later.

To produce dental prostheses, the dental laboratory technician typically duplicates the patient teeth in plaster from an impression provided by a dentist, then uses the lost wax method to realise a casting mold, then invests the mold in the casting oven filling it with metal in fusion to build the substructure components of dental prostheses, then porcelain is applied and fused on the metal substructure to complete the prosthetic work. The casting oven either uses the centrifuge effect principle or a vacuum chamber.

The lost-wax method to realise a casting mold therefore generally consists of the following steps:

1. Apply die spacer on the surface of the plaster die to emulate the cement space;
2. Realise the prosthesis out of wax (by dipping and wax-up
3. technique);
4. Add wax pouring sprue (off-the-shelf item) on top of the wax prosthesis;
5. Add several prosthetic elements with pouring sprues on top of an investment tree (off-the-shelf element or not) with an adequate casting reservoir;
6. Add wax cooling sprues and vent sprues (off-the-shelf items) when desirable;
7. Install the wax ensemble in an investment cylinder;
8. Invest the ensemble with a refractory material (heating will eliminate the wax and result in a negative mold of the ensemble: casting reservoir, tree, sprues, prosthesis).

However, the lost-wax method is labour-intensive and also requires dexterity to manipulate this fragile wax structure without breaking it, twisting it or otherwise distorting it. Furthermore, the use of off-the-shelf items constrains the design of the casting mold.

The computer-aided design and manufacturing of the prosthesis is an alternative method for producing dental prosthesis. This method is typically used in conjunction with computer-controlled milling machines. Blanks are milled into prostheses. However, with this process, a large proportion of the blank material is rejected. When the prosthesis substructure is composed of a precious alloy, the scrap metal represents more value than the prosthesis itself.

SUMMARY OF THE INVENTION

Accordingly, an object of the present invention is to provide an improved wax casting mold and method for making same.

According to a first broad aspect of the present invention, there is provided a method for producing a dental prosthesis comprising: obtaining three-dimensional digital data relating to a patient's dentition; designing a virtual prosthesis for the dentition using the three-dimensional digital data; transmitting digital data corresponding to the virtual prosthesis to an automated prototyping system; producing a prototype of the dental prosthesis with the automated prototyping system, the prototype made of a material that can be ablated; covering at least the prototype with a hardening material and removing the prototype from within said hardening material to produce a mold for the dental prosthesis; casting the dental prosthesis by filling the mold with a metal and removing the hardening material.

Preferably, the method also comprises designing virtual conduits and reservoirs to be produced with the prototype of the dental prosthesis and used in casting of the dental prosthesis. Virtual conduits and reservoirs are positioned on the prosthesis by simulation to minimise a quantity of metal needed to produce the prosthesis while improving an invested metal flow in order to fill completely the prosthesis during the casting.

Also preferably, the method comprises designing a virtual casting mold container, wherein the virtual conduits and reservoirs are configured on the virtual casting mold container to support multiple patterns in a desired casting position, provide passageways for fluid elimination, and form lines through which molten metal enters the mold.

Throughout this application, the term investment is used as a common term in the art of casting wherein investment casting designates a casting technique that uses destructible models covered in a refractory material and forming a jointless mold. The term investment casting can also refer to the lost-wax process. The process comprises pouring a metal into a mold obtained by coating a wax, plastic, or mercury gel prototype with a refractory material and removing the material using heat. The term refractory is used to mean a material or product other than metal or alloy with a pyroscopic resistance at least equal to 1500 degrees Celsius.

BRIEF DESCRIPTION OF THE DRAWINGS

These and other features, aspects and advantages of the present invention will become better understood with regard to the following description and accompanying drawings wherein.

DETAILED DESCRIPTION OF THE PREFERRED EMBODIMENT

Figure 1:
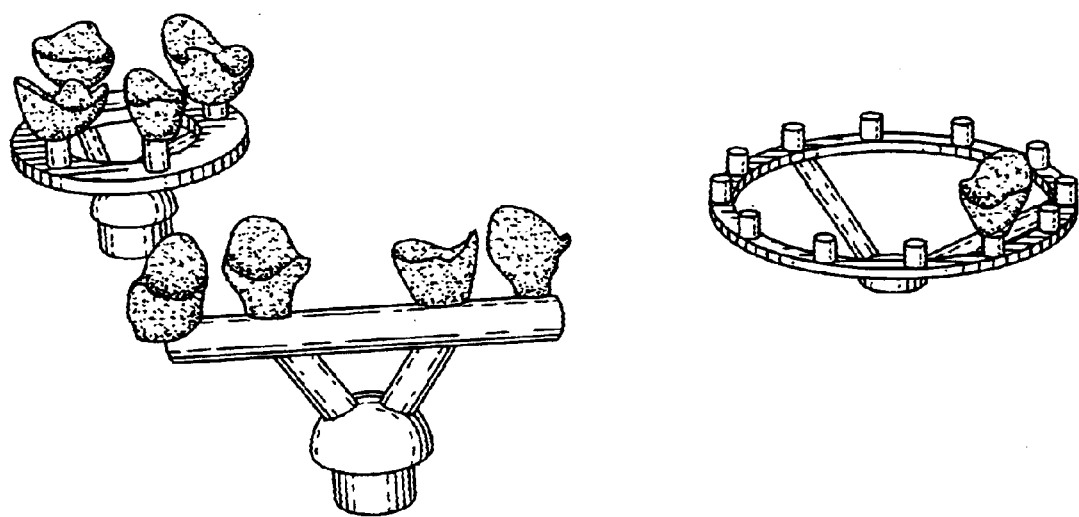
FIG. 1 is a perspective view of three wax models according to the present invention used to produce casting molds

According to the present invention, there is provided a method to design and manufacture casting molds for patterns, particularly dental prostheses and to wax models to create such casting molds. This method will be referred herein as the Waxpro™ system.

Generally stated, the method of the present invention comprises following steps:

Designing the prosthesis using computer-aided design (CAD) tools such as Cynovad's Pro 50™ scanner and CAD software;

Designing the conduits and reservoirs configuration as well as the mold container using CAD tools to support multiple patterns in the desired casting position, provide passageways for wax elimination and form lines through which molten metal enters the mold;

Realizing the designed structure using a low fusion temperature material such as wax and a rapid prototyping machine such as that of Thermojet™ by 3D System Inc.;

Invest the ensemble with a refractory material (heating will eliminate the wax and result in a negative mold of the ensemble: casting reservoir, tree, sprues, prosthesis);

Each of these steps will now be described in more detail. In step 1, quantitative data on shape of the patient's teeth is advantageously acquired by a digital 3D scanner either directly in the patient's mouth or on a model made from an impression made by the dentist; then the morphology of the prosthesis is advantageously produced using CAD software. In particular, the regularity of the coping thickness obtained with machine precision ensures that structural specifications are met with the minimal quantity of metal and no rework.

The digital measurements of the shape of teeth are obtained in a similar way as those obtained by devices and methods described in U.S. Pat. Nos. 4,611,288, 4,663,720, 4,742,464, 4,952,149, 5,092,022 and 5,237,998 which are herein included by reference. It is to be noted that other devices may also be used without departing from the spirit and nature of the present invention.

In step 2, the positioning of the prosthetic elements, the design of the conduits and reservoirs configuration given the custom-made prostheses to invest, and the casting mold external shape is advantageously produced using a computer-aided design software tool. The conduits and reservoirs are custom shaped and positioned to minimize the quantity of metal needed while improving the invested metal flow in order to fill completely the prostheses and allowing the crystallization to begin simultaneously where the highest precision is needed, thus ensuring the quality of the prosthetic work. The design is optimized given the fluid dynamics properties of the chosen metal alloy. The computer simulation of casting process provides the preferred analysis tool. The manufacturing of the ensemble (the pattern, the wax conduit and reservoir elements, the mold external wall) in a single piece allows for the precise placement of tiny fragile vent sprues close to the hot metal mass and cooling sprues close to the mold external wall. Furthermore, the pouring sprue leading to each prosthetic element can automatically be marked to identify it, as well as the casting cone and mold external wall. Finally, the mold external wall can be shaped and/or marked to indicate the optimal orientation when placed in the casting oven.

In step 3, the designed structure combining the prostheses, the conduits and reservoirs configuration, and the external wall of the mold is advantageously realized using a process such as the rapid prototyping machine of 3D System Inc. It is to be noted that other devices may also be used without departing from the spirit and nature of the present invention.

Step 4 is the same as the typical approach used by dental technicians to produce a casting mold, that is investing the designed structure with a refractory material. Vibration is used to facilitate the flow. Heating eventually eliminates the wax and results in a negative mold of the casting reservoir, sprues and prosthesis.

The accompanying figures illustrate realizations of wax models for dental prosthesis according to the present invention. More specifically, FIG. 1 illustrates three wax models constructed according to the principle of the method of the present invention in perspective view. These wax models are intended to be used to create casting molds.

Figure 2:
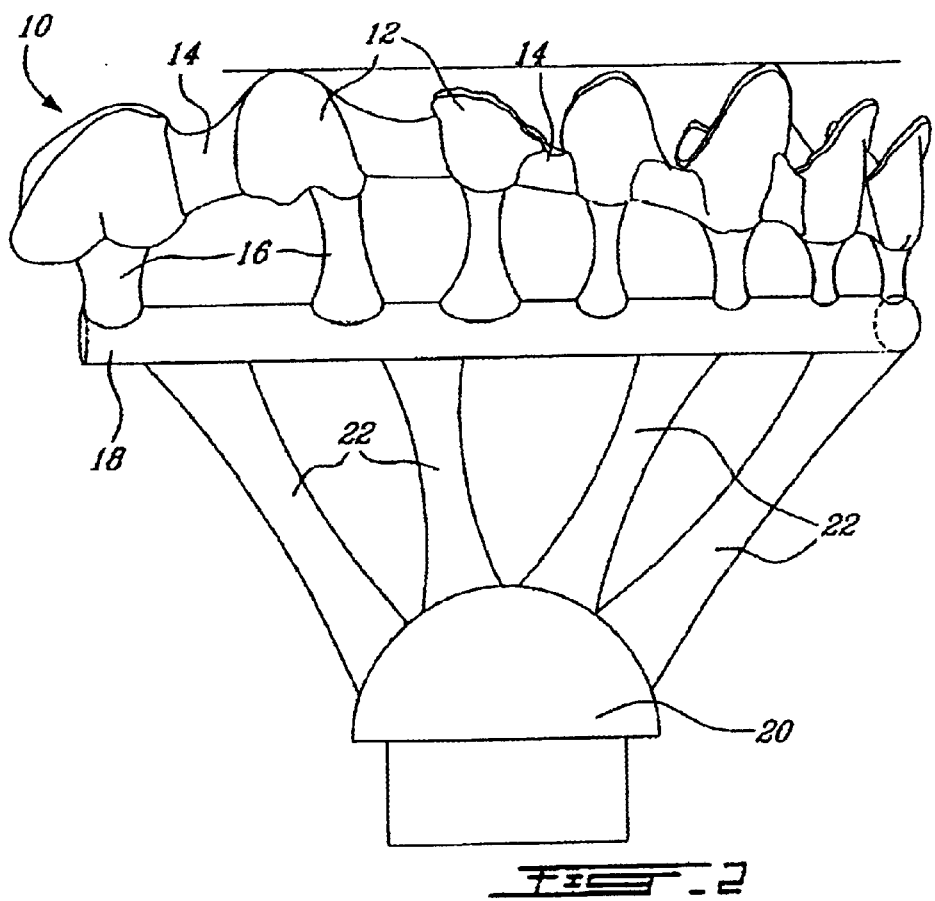
FIG. 2 is a side elevational view of a wax model according to the present invention, including several prosthesis
Figure 3:
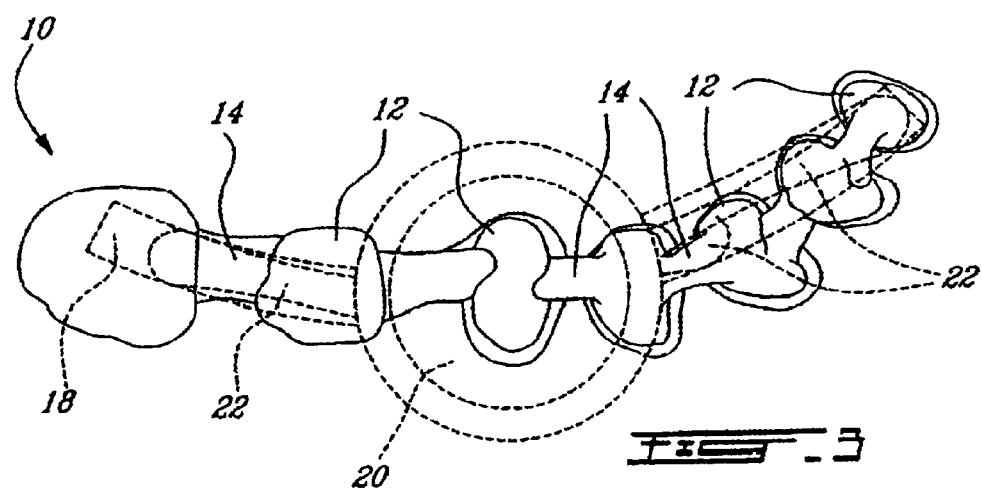
FIG. 3 is a bottom plan view of the wax model of FIG. 2

FIGS. 2 and 3 respectively illustrate side elevation and bottom plan views of a wax model 10 comprising a plurality of prostheses 12 interconnected by connectors 14. The prostheses 12 are mounted on individual sprues 16 connected to a reservoir 18 itself connected to a master inlet 20 via primary sprues 22.

As will easily be appreciated by one skilled in the art, the use of a computer modeling tool allows the design of custom investment trees suited for the number, dimensions and position of the dental prosthesis. Furthermore, it allows a perfect positioning of the prostheses with respect to the reservoir to thereby improve the success rate of the casting steps.

An advantage of the WaxPro™ system compared to the traditional way is the time saving linked with the automation of many steps involved in the processes that are carried in parallel: for example, it is possible to start scanning the next batch of prostheses and creating the CAD models while the waxing machine is making previous ones. A waxing machine, like the ones used in the rapid prototyping field, is also capable to make several ensembles (conduits, reservoirs, and prostheses) in a single session.

Another advantage of the WaxPro™ system is that it does not require the dental laboratory technician to go through a long and tedious manual procedure in which the manipulation of fragile wax pieces can be awkward and yield a significant percentage of costly remakes. The computer-aided design of the conduits and reservoirs ensemble minimizes the quantity of precious alloy needed, thus cost, and it prevents cavities resulting from bubble formation during the casting step thus avoiding another cause of remakes. The CAD system automatically provides the precise quantity of metal needed, time is saved. Yet another advantage of the Waxpro™ system is the referencing of the different prosthetic elements and the different casting mold; this feature also to save time after and ease quality control.

Finally, this system gives a more controlled result in, for example, the regularity of the thickness of the prosthesis obtained. The resulting quality saves time and precious metal after by avoiding lengthy polishing step before applying the porcelain.

To design the wax model, a digital library of predefined investment trees is used. Of course, the system allows the user to create his own tree via a "tree edition software" where the user can change different parameters of dimension, diameter of the different parts of the tree, size of the reservoir, so it is customized every time depending on the shape of the parts (simple copings, bridges, etc . . . ) and the metal that will be used for casting. An expert system may also be used to determine the optimum dimensions of these elements according to the prosthesis to be made.

Figure 4:
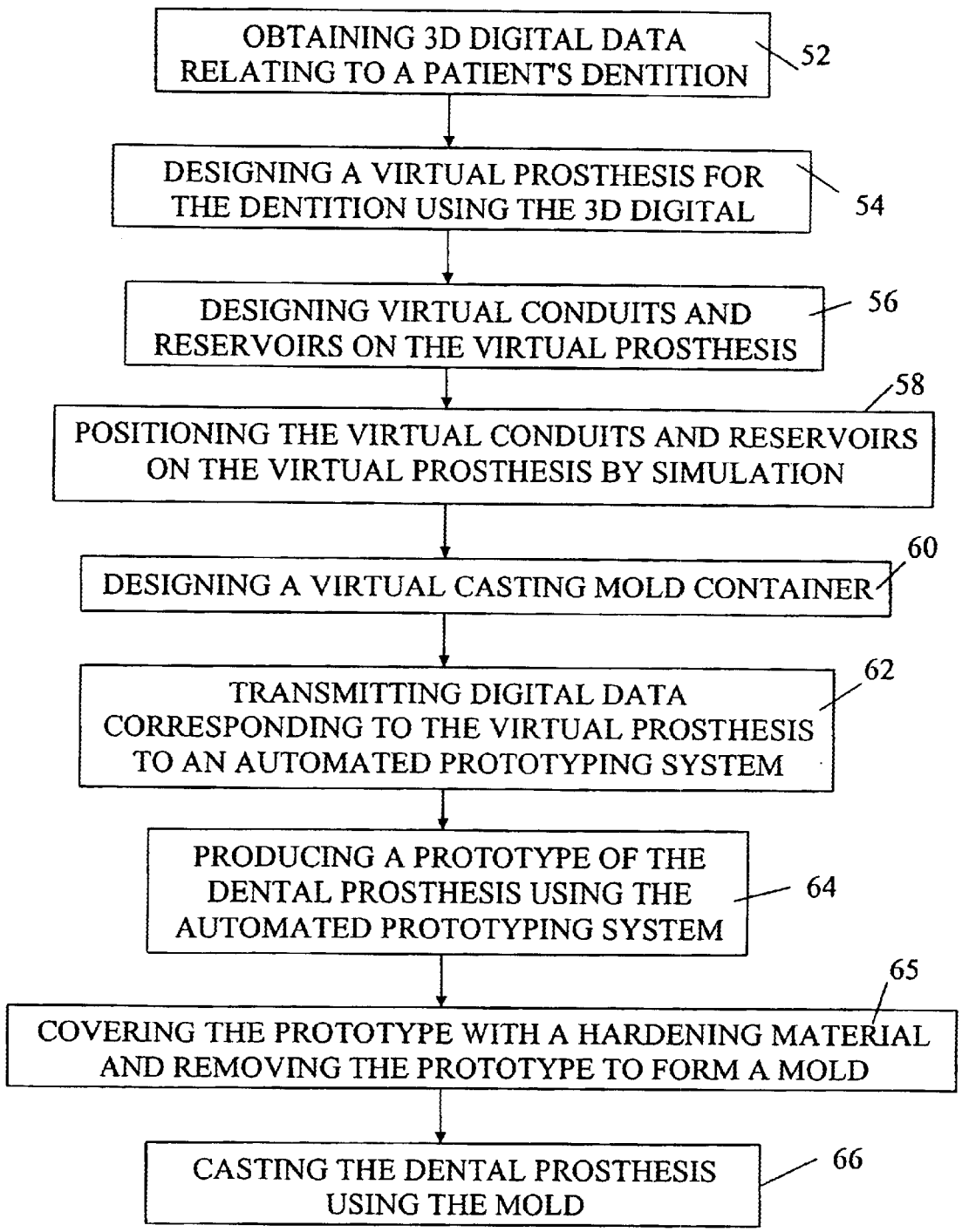
FIG. 4 is a flow chart in accordance with the present invention.

FIG. 4 describes the steps according to the method of the present invention. The first step is to obtain the three-dimensional digital data relating to the patient's dentition 52. This can be done by taking an imprint of the patient's mouth and scanning the model, or by scanning directly in the patient's mouth the entire dentition. A virtual prosthesis is then designed for the dentition using the three dimensional digital data previously acquired 54. Computer aided design (CAD) software is used for designing the virtual prosthesis. Additionally, virtual conduits and reservoirs are also designed on the virtual prosthesis 56. The virtual conduits and reservoirs are positioned on the virtual prosthesis through simulation 58. Simulation of the casting is done to determine the optimal placement of the conduits and reservoirs on the prosthesis. A virtual casting mold container is also designed using the CAD software 60.

Once all the different aspects of the prosthesis have been designed virtually, all of the corresponding virtual data is transmitted to an automated prototyping system 62. The prototype is then produced for the dental prosthesis using the automated prototyping system 64. A hardening material is used to cover the prototype and the prototype is removed from inside, producing a new mold 65. The new mold is then used in casting the dental prosthesis 66.

It is to be noted that a computer aided design system such as that described above can be coupled with an automated prototyping system such that the rapid-prototyping is done directly in a dental material. The prosthesis would then require some post-processing and be ready to be installed in a patient's mouth.

It can be appreciated that forming a model of a patient's dentition including surfaces corresponding to the dental structure nearby the location that the dental prosthesis is to be placed in the mouth of a patient is equivalent to taking a dental imprint of the mouth. It can also be appreciated that the method according to the present invention and as described above covers the following steps: scanning surfaces of the model to collect three dimensional digital data corresponding to the surfaces of the dental structure; displaying on a monitor screen of computer aided design equipment an image of a proposed dental prosthesis based, at least in part, on the collected three dimensional digital data corresponding to the surfaces; with the aid of the computer aided design equipment, modifying the image so that the image displayed on the monitor screen substantially corresponds to the dental prosthesis to be manufactured; collecting the three dimensional digital data substantially corresponding to the image of the dental prosthesis to be manufactured and transmitting the three dimensional digital data of the image of the dental prosthesis to be manufactured to automated prototyping equipment; using the automated prototyping equipment making from a wax material the pattern of the dental prosthesis to be manufactured based upon the three dimensional digital data substantially correspond to the image of the dental prosthesis to be manufactured; and using the pattern in the lost wax investment casting process manufacturing the dental prosthesis.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

We claim:

1. A method for producing a dental prosthesis comprising:

obtaining three-dimensional digital data relating to a patient's dentition;

designing a virtual prosthesis for said dentition using said three-dimensional digital data;

transmitting digital data corresponding to said virtual prosthesis to an automated prototyping system;

producing a prototype of said dental prosthesis with said automated prototyping system, said prototype made of a material that can be ablated;

covering at least said prototype with a hardening material and removing said prototype from within said hardening material to produce a mold for said dental prosthesis;

casting said dental prosthesis by filling said mold with a metal and removing said hardening material.

2. A method as claimed in claim 1, further comprising designing virtual conduits and reservoirs to be produced with said prototype of said dental prosthesis and used in said casting said dental prosthesis.

3. A method as claimed in claim 2, wherein said step of designing comprises simulating metal flow and crystallisation in said mold to determine a simulated structure of said prosthesis, and said virtual conduits and reservoirs are positioned on said prosthesis using said simulation to minimise a quantity of metal needed to produce said prosthesis while improving a metal flow in order to fill completely said prosthesis during said casting.

4. A method as claimed in claim 3, wherein said virtual conduits and reservoirs are positioned to support multiple patterns in a desired casting position, provide passageways for fluid elimination, and form lines through which molten metal enters said mold.

5. A method as claimed in claim 3, wherein said simulation is optimised by considering fluid and thermal dynamic properties of a chosen metal alloy.

6. A method as claimed in claim 2, further comprising designing a virtual casting mold container, wherein said virtual conduits and reservoirs are configured on said virtual casting mold container.

7. A method as claimed in claim 6, wherein said producing a prototype further comprises producing said prototype in one piece.

8. A method as claimed in claim 6, wherein said virtual casting mold container is one of marked and shaped to indicate an optimal orientation when said prototype is placed in a casting oven.

9. A method as claimed in claim 2, wherein each of said virtual conduits and reservoirs is marked to identify it.

10. A method as claimed in claim 1, wherein said three-dimensional digital data is acquired by scanning said dentition directly in a patient's mouth.

11. A method as claimed in claim 1, wherein said designing a virtual prosthesis further comprises using a digital library of predefined investment trees.

12. A method as claimed in claim 1, wherein said designing a virtual prosthesis further comprises creating an investment tree using a tree edition software.

13. A method as claimed in claim 1, wherein said prototype is made of wax.

* * * * *